United States Patent [19]
Lorenz

[11] Patent Number: 5,841,534
[45] Date of Patent: Nov. 24, 1998

[54] APPARATUS FOR DETERMINING THE DENSITY, SIZE OR SIZE DISTRIBUTION OF PARTICLES

[75] Inventor: Gerhard Lorenz, Katlenburg-Lindau, Germany

[73] Assignee: Gerhard Lorenz Innovative Technik + Messgerätebau, Katlenburg-Lindau, Germany

[21] Appl. No.: 732,307
[22] PCT Filed: Apr. 21, 1995
[86] PCT No.: PCT/EP95/01521
  § 371 Date: Jan. 13, 1997
  § 102(e) Date: Jan. 13, 1997
[87] PCT Pub. No.: WO95/29393
  PCT Pub. Date: Nov. 2, 1995

[30] Foreign Application Priority Data

Apr. 22, 1994 [DE] Germany ............ 44 14 166.1

[51] Int. Cl.⁶ .......... G01N 21/00; G01N 15/02; G08B 17/10
[52] U.S. Cl. .......... 356/336; 356/338; 356/340; 356/342; 250/564; 250/574; 340/630; 340/638; 340/555
[58] Field of Search .................. 356/335–343; 250/564, 574; 340/630, 638, 555

[56] References Cited

U.S. PATENT DOCUMENTS

| | | | |
|---|---|---|---|
| 4,397,557 | 8/1983 | Herwig et al. | 356/342 |
| 4,607,915 | 8/1986 | Cole . | |
| 4,906,978 | 3/1990 | Best et al. | 356/439 |
| 5,231,378 | 7/1993 | Dennis et al. | 356/338 |
| 5,440,145 | 8/1995 | Cole | 356/336 |
| 5,587,790 | 12/1996 | Nagashima | 356/338 |

FOREIGN PATENT DOCUMENTS

| | | | |
|---|---|---|---|
| 0463795 | 1/1992 | European Pat. Off. | 356/338 |
| 3334545 | 9/1983 | Germany . | |
| 4-260197 | 9/1992 | Japan . | |
| WO 93/08461 | 4/1993 | WIPO | 356/336 |

Primary Examiner—Frank G. Font
Assistant Examiner—Jason D. Vierra-Eisenbey
Attorney, Agent, or Firm—Thomas, Kayden, Horstemeyer & Risley

[57] ABSTRACT

A device is disclosed for measuring light scatter by particles (3) suspended in a carrier medium with a view to ascertaining the density, size or size distribution of the particles. The device comprises: at least one light source (8) which directs light onto a light-scattering center (2) in the carrier medium with the suspended particles (3); a receiver (4) to pick up a portion of the scattered light from the light-scattering center; and an evaluating device connected downstream of the receiver (4). The invention provides for an elongated detection chamber bounded radially around its central axis by the wall of a housing (1) which also acts as a duct for the through-flowing carrier medium with the suspended particles (3). Each light source (8) is mounted on the wall of the housing (1) and points toward the central axis of the detection chamber. The receiver is coaxial with the detection chamber and includes a sensor and a diaphragm system (6, 7) which is designed in such a way that the wall of the housing (1) surrounding the light scattering center (2) is excluded from the field of view of the sensor.

13 Claims, 4 Drawing Sheets

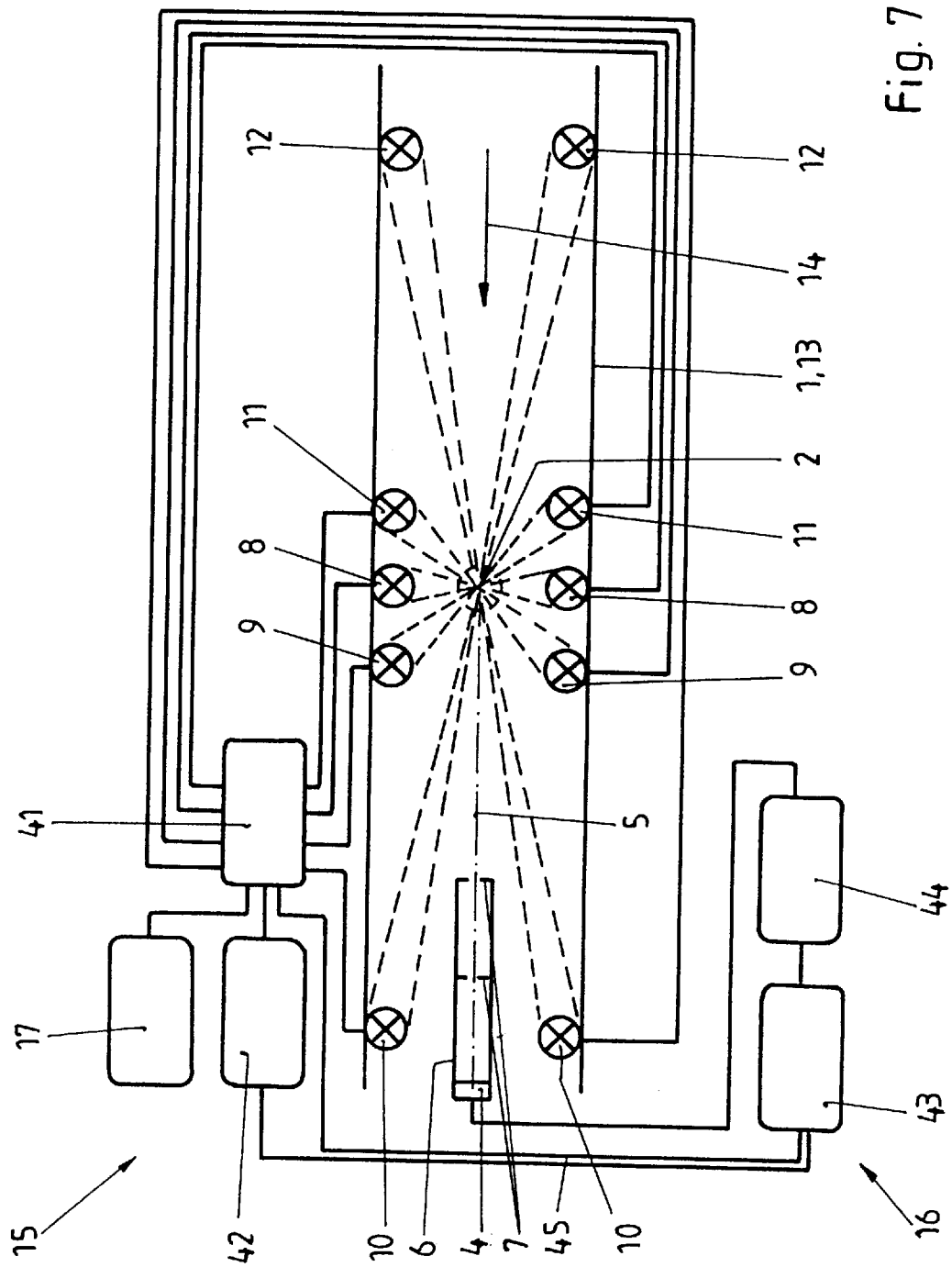

5,841,534

APPARATUS FOR DETERMINING THE DENSITY, SIZE OR SIZE DISTRIBUTION OF PARTICLES

FIELD OF THE INVENTION

The invention relates to an apparatus for measuring the light scatter by particles suspended in a carrier medium for determining the density, the size or the size distribution of the particles.

BACKGROUND OF THE INVENTION

Besides measuring the light absorption, measuring the light scatter is a generally known method to detect suspended particles in air but also in other gases or also in transparent liquids like, for example water and to determine the density, the size or the size distribution of the particles. In this, light from a monochromatic or polychromatic light source is directed towards the carrier medium. The beam of light hits the particles suspended in the carrier medium and is absorbed afterwards preferably in a light trap. If the beam of light hits a particle, the particle deflects a small portion of the light, as a so-called scattered light, out of its original direction. A light sensitive receiver measures the intensity of the scattered light. The spatial intersection region which is covered both by the beams of light from the light source and the angle of view of the receiver is called light-scattering center here.

JP 4-260 197 A in US-periodical: Patent Abstracts of Japan, Section P, Vol 17/No. 48 (1993) P-1477 shows an apparatus in which beams of light pulsed chronologically one after another are directed from two light sources towards a common light-scattering center for determining the size (diameter) of particles suspended in a carrier medium. A common receiver is associated with both light sources, the axis of the receiver is pointed at the light -scattering center. The two light sources can be arranged in such a way that they emit their beams of light at different angles to the axis of the receiver.

Both light sources are arranged in such a way that the receiver receives the scattered light in forward direction. The signals supplied by the common receiver are supplied to an evaluating device having a control device for the timing of the pulsed beams of light one after another.

It remains open whether and, should it be, how the carrier medium flows or is guided. Additionally, the device is depicted in a way in that no special housing is provided, so that problems which are associated with the occurrence of light scattered at an inner wall of a housing and/or the accuracy of the measurement which is hence affected are consequently not mentioned.

DE 38 31 654 A1 shows and describes an optical smoke alarm with a strongly light absorbing measuring chamber. With little effort it shall be avoided that the scattered radiation caused by fouling of the measuring chamber leads to a false alarm. To this end, a additional second light sensitive receiver is employed in a housing-like measuring chamber, the view field of the second receiver is pointed at a surface area of the measuring chamber which is illuminated by one of the light sources. With this second receiver a comparative value is determined which corresponds to the level of fouling of the housing increasing with time, and which is appropriately taken into account in the control circuitry to eliminate the negative effects of a changing scatter radiation background in the housing on the accuracy of the measurement.

DE 33 34 545 A1 also shows an optical smoke alarm having two light sources which are arranged symmetrically to the axis of a receiver and which emit their beams of light at an acute angle to the axis of the receiver, so that the scattered light is received as backward radiation here. The two light sources and the receiver are contained in a housing having two openings through which the beams of lights from the light sources can emerge, so that the problem of wandering reflected scatter light radiation is thus solved without using lots of diaphragms. The carrier medium with the particles can also be fed into the housing through one of the openings.

Further apparatus have been described by Bol, Roth und Wurzbacher "Erfassung und Untersuchung kolloider Luft- und Abwasserverunreinigungen durch Streulichtmessung", published in Batellebericht 1969, pages 23–29. There, a single light source in form of a laser is used, the beam of light of which is directed towards a light-scattering center through a combination of lenses and diaphragms. The carrier medium loaded with the particles flows diagonally at 90° through the light-scattering center. The beam of light is caught in a light trap. Via deviation mirrors and further lenses and diaphragms the light scattered by the particles in the light-scattering center is supplied to a receiver which is formed as a secondary electron multiplier. With this known apparatus the size of the particles suspended in the carrier medium can be determined. The apparatus operates in forward direction of the beam of light, i.e. the scattered light emitted in forward direction at a relative small angle to the axis of the beam of light is received by the receiver. The intensity of the light scattered by a particle is angle-dependent. Here, the size of the particles is an important factor. In Case of particles, which are substantially larger than the wave length of the beam of light, nearly all scattered light is emitted in forward direction. A backward scatter does actually not occur. The highest intensity is detected at relative small angle r s of the scattered light to the forward direction of the beam of light. In case of particles, the size of which is comparable to the wave length, a forward scatter and a comparatively less intensive backward scatter occur. However, the cone of light scattered in forward direction is shorter and wider than the cone of light scattered by particles, the size of which is substantially larger than the wave length. At last, in case of particles the diameter of which is substantially smaller than the wave length of the light beam, it is valid that the scattered light is emitted with the same intensity in all directions in space. The known apparatus operates with a single light source and its beam of light of fixed wave length, wherein the angle at which the receiver is arranged relative to the direction of the beam of light is also fixed. Therefore, the known apparatus is more or less suitable for different sizes or size distributions of the particles. In many cases the measuring accuracy is insufficient.

SUMMARY OF THE INVENTION

It is the problem of the invention to provide a method and an apparatus by means of which the density, the size and/or the size distribution of the particles suspended in a carrier medium can be determined, despite the use of simple constructed elements, with a high accuracy over a relative large range of different diameters and concentrations of the particles. Hence, the apparatus shall be of simple construction and producible at low cost.

According to the invention this is achieved by an influence of scattered light wandering in the detection chamber on the measuring result is prevented by means of the application of most simple constructional measures. The receiver is contained within the housing, but it is virtually pointed in the direction of the central axis of the elongated detection chamber into a black hole behind the light-scattering center. Thus, in the new apparatus a fouling of the wall of the housing, a light source which does not solely concentrate its beams of light on the light-scattering center, and an incomplete absorption of the beams of light after them emerging from the light-scattering center are not critical. This allows the use of economical construction elements, especially in case of the housing and the light source.

The receiver arranged within the housing is not necessarily a photo sensor converting the scattered light into a signal which is normally electrical but a device collecting the scattered light to be converted into the signal. This device for collecting the scattered light and hence the receiver in the narrow sense of the invention can also be, for example, the entrance surface of a light guide guiding the collected scattered light to a photo sensor arranged outside the housing.

The elongated detection chamber is preferably axisymmetric or rotational symmetric around its central axis. Ideally, it is round, and it is then bounded by a tube section being round in cross-section as the housing, whereby the new apparatus can be produced economically.

The diaphragm system according to the invention can also comprise optical diaphragms, i.e. lenses. However, lenses are neither necessary nor preferred as parts of the diaphragm system as they increase the constructional effort for the new apparatus.

In an enhanced version, the invention is based on the common knowledge to use not only beams of light from a single light source but beams of light from several light sources and to direct these beams of light pulsed chronologically one after another, i.e. for a predetermined interval of time, towards separate or one common light-scattering center (s). To this end, relatively simply constructed light sources which are very economical and which do not require a combination of lenses and diaphragms themselves can be used in the new apparatus. Preferably, just one single receiver is associated with these several light sources or their beams of light, respectively, wherein it is possible to realize different relative arrangements between the beams of light of each single light source and the axis of the receiver.

It is possible to cover the forward scatter as well as the backward scatter. The scatter light impulses which come chronologically one after another from the particles are received by a common receiver, stored and evaluated, wherein it is important to record the assignment of each scattered light impulse to the respective light source. Hence, it possible to receive the scattered light under different angular relations. Individual relations between the light sources and the receiver may be selected depending on the application. In case of a fully unknown particle size and an unknown size distribution all light sources should be operated. Hence, the whole range of angle can be virtually covered, and it is possible to construct a so to speak universal light scatter measurement implement which combines the advantages of the different individual light scatter measurement implements known up to now, which measure either in specific forward regions or in specific backward regions.

Herein, it is particularly advantageous if beams of light are directed towards the separate light-scattering center or the common light-scattering center at different angles and/or with different wave lengths. It is appreciated, that the scatter light impulses are here also received chronologically offset one after another by the common receiver.

Beams of monochromatic light may be use, hence for example, from laser diodes.

In case of a common light-scattering center, the chronological consecution of the pulsed beams of light is preferably fast compared to the flow velocity of carrier medium with the particles through the light-scattering center. In this way it is possible to direct a whole series of beams of light towards one particle and to receive the scattered light impulses from this particle.

In case of several light-scattering center, their spatial and temporal distance with regard to the consecution of the beams of light are preferably suited to the flow velocity of the carrier medium with the particles through the detection chamber.

With the new apparatus it can be made use of a plurality of beams of light from light sources associated with a single receiver in a way which is known as such, wherein different relative spatial arrangements between light source and receiver can be realized most readily. In turn, the receiver receives only a portion of the scattered light from the light-scattering center, i.e. the angle of view of the receiver does only covers a narrow angular region of the scattered light emitted out of the light-scattering center.

The light sources can not only be arranged in a plurality but also at different angles to the axis of the receiver, if this is useful in the actual application. It is also possible to construct an universal apparatus in which just a part of the realized light sources or all light sources can selectively be used. Particularly, monochromatic light sources are provided which emit pulsed beams of light of different wave lengths. Here also, the control device can make a selection with regard to the usage of the light sources which are useful in the actual application.

Particularly, laser diodes and light emitting diodes can be provided as light sources. A combination of both light sources can also be useful in certain applications.

Also, two common receivers can be provided in the elongated detection chamber, which are directed in opposite directions towards the light-scattering center, so that they can receive the scattered light of a single light source from the light-scattering center on the one hand in forward direction and on the other hand in backward direction. Despite from being orientated face to face, both receivers view in the direction of the axis, and hence, virtually into a black hole. Wandering scatter light radiation and/or reflected light radiation can normally have no negative effect on the accuracy even in case of two receivers as long as it is not just reflected by the receiver on the opposite side. The number of necessary light sources can be divided by two in case of the two receivers orientated face to face. Receiving the scattered light by the two receivers can take place at the same time, wherein both pulses must however be distinguished and, as a rule, be further processed separately.

BRIEF DESCRIPTION OF THE DRAWINGS

The invention will be further explained and described by means of embodiment examples of the new apparatus.

FIG. 7 a block diagram for an universal light scatter measuring implement.

DETAILED DESCRIPTION

Figure 1:
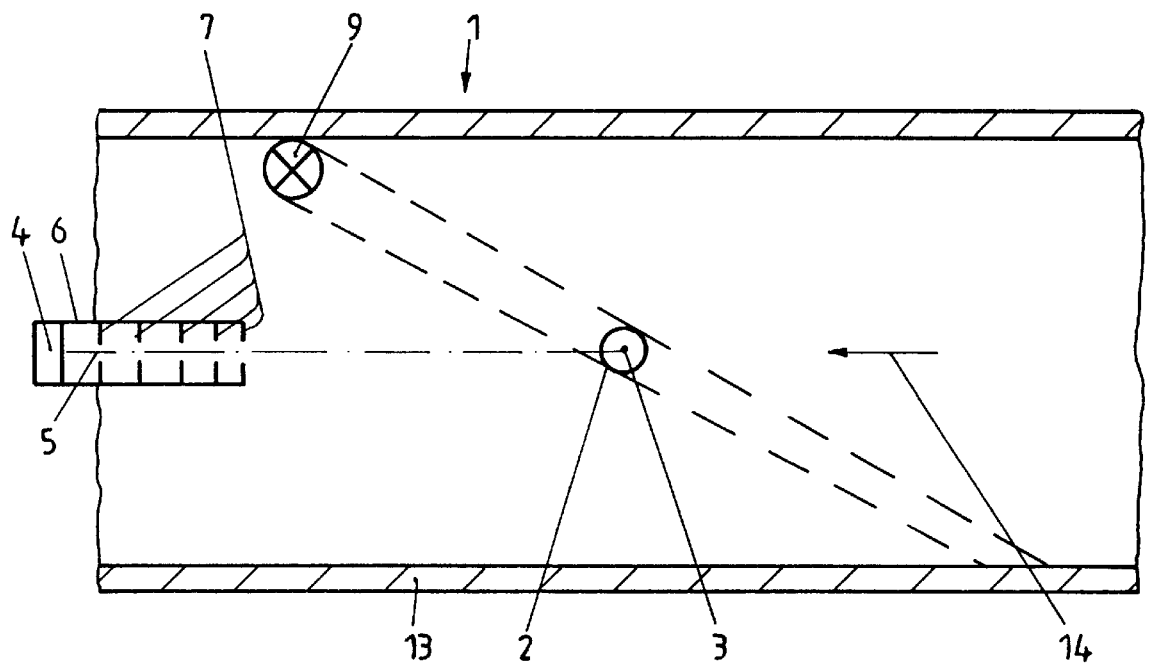
FIG. 1 shows a schematized arrangement of the light source relative to the receiver in the detection chamber.

In FIG. 1, a tube-like housing 13 is depicted the wall of which bounds an elongated detection chamber radially around the central axis of the detection chamber. A light-scattering center 2 is located on the central axis of the detection chamber, a particle 3 may be in the central point of the light-scattering center 2 or somewhere else within the light-scattering center. A carrier medium in which the particle 3 is suspended flows through the tube-like housing parallel with the central axis in direction of arrow 14.

A receiver 4 is arranged coaxially with the central axis of the detection chamber, so that its axis 5 is directed towards the light-scattering center 2. The receiver 4 is included in a receiver housing 6 in which diaphragms 7 are arranged towards the light-scattering center to restrict the view field of the receiver provided at the other end or the receiver housing 6 so that it does not cover the wall of the housing 1. Even though only one or two diaphragms distributed over the receiver housing are represented in the FIGS. 2 to 7, the view field of the receiver is restricted to a narrow region around the central axis of the detection chamber here also.

According to FIG. 1 a single light source 9 is associated with the receiver 4, the beams of light from the light source 9 intersect the view field of the receiver 4 in the light-scattering center 2.

Figure 2:
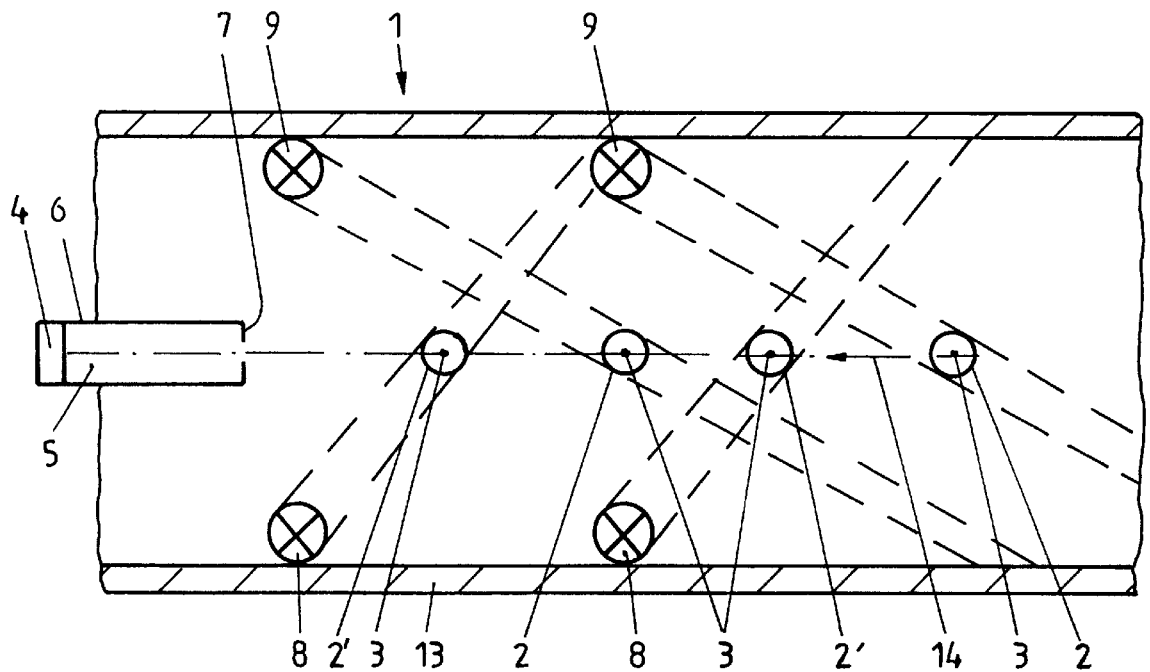
FIG. 2 shows a first schematized arrangement of several light sources relative to the receiver in the detection chamber.

According to FIG. 2 four light sources 8 and 9 are provided the beams of light of which intersect the field of view of the receiver 4 in four light-scattering centers 2 and 2'. Herein, the angles between the beams of light from the light sources 9, which intersect the field of view in the light-scattering centers 2, and the axis of the receiver are equal just as the angles of the beams of light from the light sources 8 which intersect the field of view in the light-scattering centers 2'.

Figure 3:
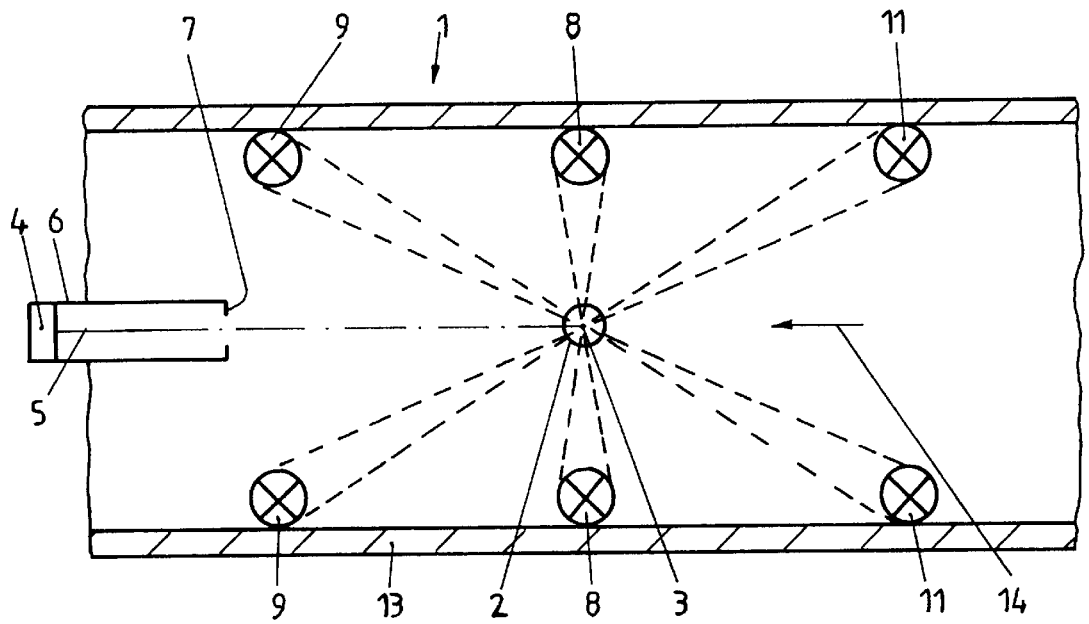
FIG. 3 shows a second schematized arrangement of several light sources relative to the receiver in the detection chamber.

According to FIG. 3 a plurality of light sources associated with the single receiver 4 is distributed over the circumference of the tube-like housing 1, the beams of light from the light sources being directed towards a common light-scattering center 2. Two light sources 8 are provided, the axes of the beams of light from the light sources 8 which are directed towards the light-scattering center 2 are arranged perpendicularly to the axis 5 of the receiver 4 and to the axis of the tube-like housing 1. Two further light sources 9 are provided at an acute angle for the backward scatter measurement; this means, that the receiver 4 receives scatter light impulses of the backward scatter at an acute angle relative to the direction of the light beams emitted from the light sources 9 onto the light-scattering center 2. Further light sources, which are also used for the registration of backwardly scattered light, can be distributed over the wall of the tube-like housing 1. Two further light sources 11 which receive a portion of the forwardly scattered light are provided virtually on the other side of the plane defined by the plane of the beams of light from the light sources 9. This means, that the axes of the beams of light emitted from the light sources 11 towards the light-scattering center, together with the axis 5 of the receiver 4, define a further angle in forward direction. Further light sources can be provided on this side. They are also used for the registration of the forwardly scattered light. It is appreciated, that the intensity of the scattered light reaching the receiver 4 can be increased for each light-scattering angle in that the number of light sources 8, 9 or 11 is increased. For each angle or range of angle, respectively, a multitude of light sources either of equal or of different wave length can be arranged rotational symmetric around the axis 5 of the receiver 4.

As explained, the housing 1 is formed by a tube section 13 through which the carrier medium with the floating particles flows in direction of an arrow 14. Although only two light sources 8, 9 or 11 are depicted in the FIGS. 2 and 3, it is appreciated, that a plurality of each kind of light source 8, 9 or 11 can be arranged along the wall or over the circumference of the tube section 13 in the respective plane. The axis 5 of the receiver 4 is also the central axis of the detection chamber bounded by the tube section 13. The light sources 8, 9, 11 are directed towards separate or one common light-scattering center (s) 2. Therein, at least in case of different light sources or different angles of the beams of light to the axis 5 of the receiver 4, the light sources 8, 9, 11 are switched on and off in a fixed order to generate light impulses directed towards the light-scattering centers 2 and to enable receiving and evaluating scatter light impulses from the light-scattering center 2 on the receiver 4.

An evaluating device, not shown, which is connected downstream of the receiver 4 is associated with the elements of the apparatus depicted in FIGS. 1 to 3. In the simplest case, if the apparatus is for surveying the constancy of the concentration of the particles or of the size distribution of the particles in the carrier medium, for example in operation as a smoke alarm, or if the apparatus is used for measuring the separating capacity of submicron particulate filters, a relative slow change-over switch forming a part of the evaluating device is sufficient by which certain combinations of the light sources can also be switched on. In so far a scatter light measurement can be performed in which only the light sources 8 are switched on. Alternatively, if only the light sources 11 are operated, a scatter light measurement in forward direction can be performed. In a scatter light measurement in backward direction only the light sources 9 are operated. Combinations of the light sources can be selected and operated in this way.

Figure 4:
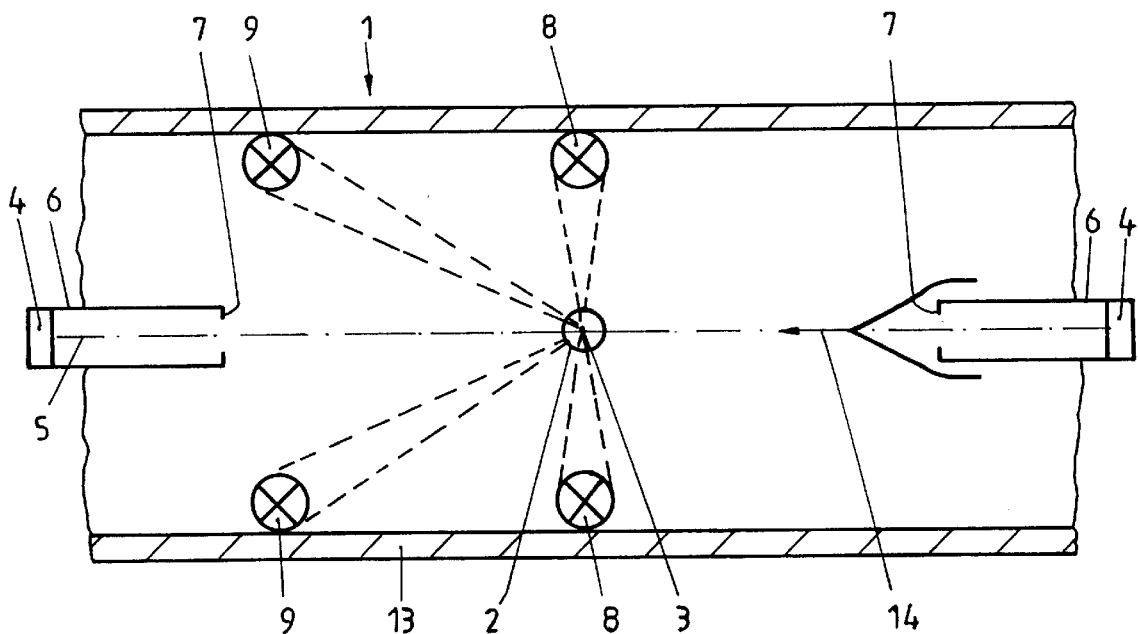
FIG. 4 a schematized arrangement of several light sources relative to two receivers in the detection chamber.

FIG. 4 shows a modified arrangement. Two receivers 4 are provided with their receiver housings 6 symmetrically arranged face to face, both receivers being directed towards a common light-scattering center 2. In comparison with the arrangement according to FIG. 3 the light sources 11 are missing. One of the receivers 4 measures the scattered light from the light sources in backward direction, the other receiver 4 in forward direction. It is appreciated, that the number of receivers 4 is doubled but light sources can be eliminated, particularly, if a plurality of light sources at different angles is provided. Here also, the receivers 4 view in the direction of the axis 5, and hence, are virtually pointed into a black hole, so that the accuracy of the measurement is not reduced by wandering scatter light radiation and/or beams of light reflected in the housing.

Figure 5:
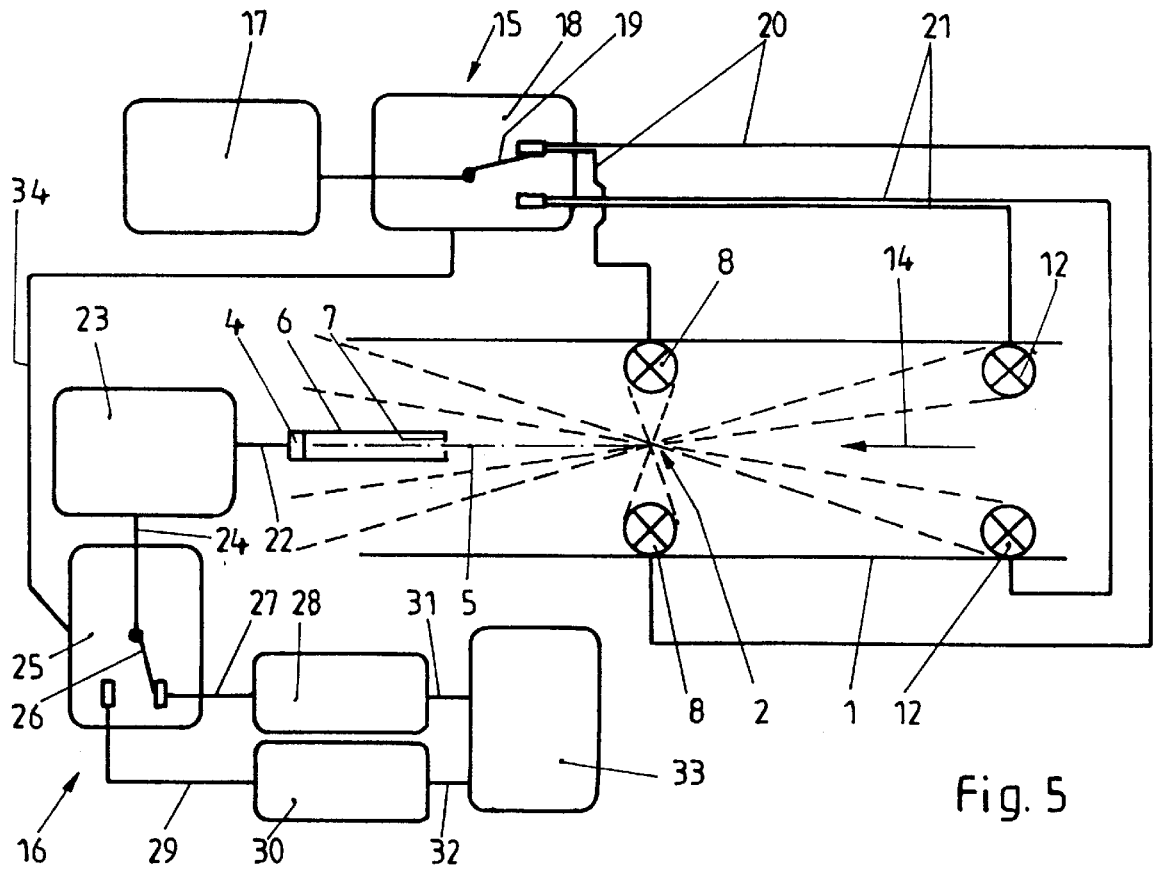
FIG. 5 a block diagram of an evaluating device in combination with the apparatus according to FIG. 3 to realize a smoke alarm.

In FIG. 5, an associated control device 15 as well as the relevant parts of an evaluating device 16 are depicted and elucidated as an example for a smoke alarm. The control device 15 comprises a electrical power supply unit 17 and connected to that a change-over automatic 18 having a switch 19 with which the light sources 8 for a 90°-measurement or further light sources 12 for a 20°-forward measurement can be alternatively switched on via corresponding lines 20 and 21. Via a line 22, the receiver 4 is connected with an amplifier 23 from which a line 24 runs to an change-over automatic 25 which is part of the evaluating device 16. The change-over automatic 25 also has a switch 26 for switching the received scatter light impulses. A limit indicator 28 connected via line 27 is suited to the 90°-scatter. A line 29 runs to a limit indicator 30 which is suited to the 20°-forward scatter. Lines 31 and 32 run from the limit indicator 28 or 30, respectively, to an alarm device 33 to indicate smoke generated in case of fire. A line 34 connects both change-over automatics 18 and 25 and cares for an appropriate synchronization so that the beams of light emitted by the light source 8 or 12, respectively, can be assigned to the corresponding scatter light impulses received by the receiver 4. In this embodiment example the two change-over automatics 18 and 25 permanently change-over between the light sources 8 and 12 at a frequency of, for example, 1 Hz. The air pollution in the range of submicron particles is determined via scatter light impulses of beams of light from the light sources 8. With the start smoldering fire, for example, very fine smokes are generated, to which the limit indicator 28 responds and in so far triggers the alarm device 33. Contrarily, if both limit indicators 28 and 30 respond at the same time, another alarm signal can be triggered off via the alarm device 33, as the existence of particles being larger in diameter can be inferred from the scatter light impulses of the beams of light from the light sources 12, these particles may come from another dust source which did not occur because of a fire. In so far it is possible to distinguish between different sources of the dusts, FIG. 6 elucidates the application of the apparatus as an aerosol photometer for filter testing. Here, only light sources 11 the beams of light from which are directed towards the light-scattering center at an angle of 45° are provided in combination with the apparatus according to FIG. 1. Light traps 35 are realized at the housing 1 in an corresponding relative arrangement. The control device 15 comprises an electrical power supply 17 for the light sources which are fed via lines 36. A line 37 runs from the amplifier 23 of the evaluating device 16 to a digital voltmeter 38, and a line 39 runs to a printer 40.

Figure 6:
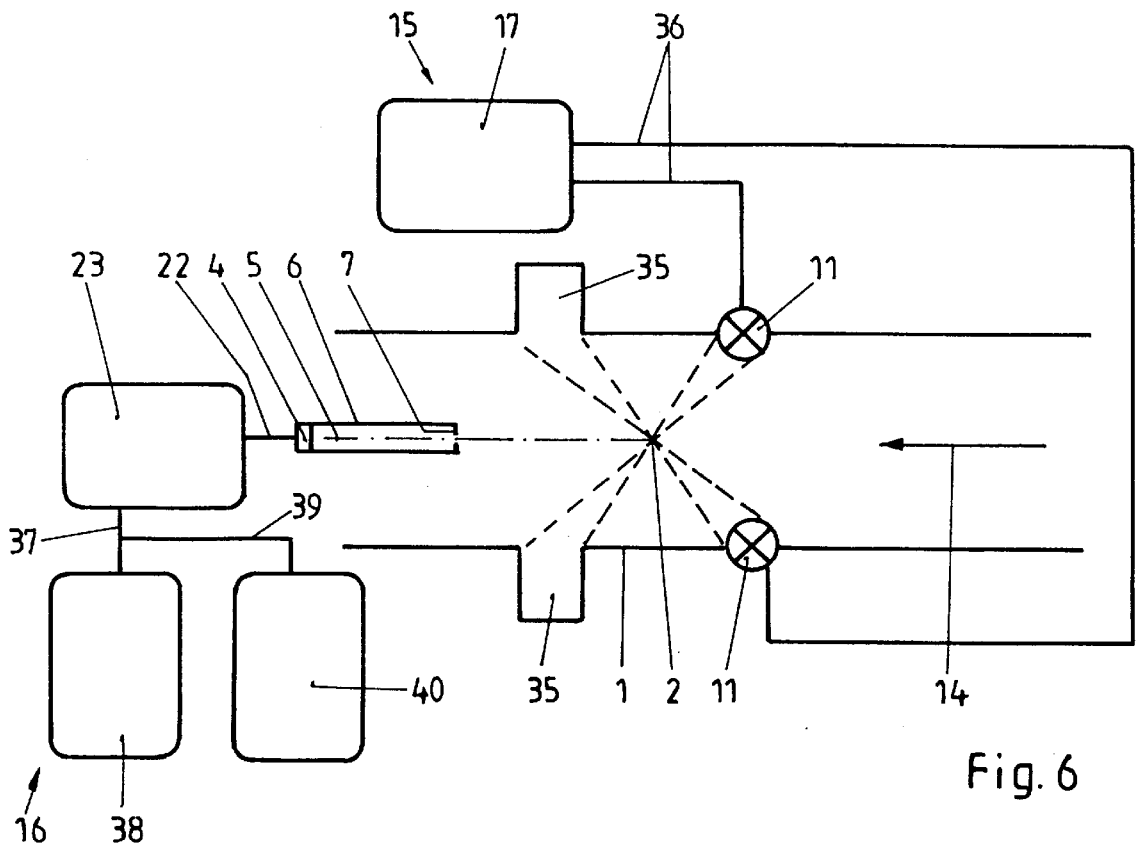
FIG. 6 a block diagram to realize an aerosol photometer for filter testing.

With this apparatus according to FIG. 6 a filter testing with a test aerosol can be performed, for example. Paraffin oil mist having a known particle size distribution and a defined index of refraction can be used as the test aerosol. Hence, the photometer just has the purpose to determine the concentration of the aerosol. To this end, the light sources 11 are used which are arranged as monochromatic light sources and which are arranged on the circumference of the housing 1 radial symmetrically around the tube axis which also is the axis 5 of the receiver 4. Although only two light sources 11 are depicted, it is appreciated, that their number is higher than two and that the light sources 11 are distributed over the circumference of the tube-like housing 1. Due to their high light intensity laser diodes can be used as light sources. Here also, the light sources 11 are focused on the common light-scattering center 2 and generate a high luminance by which even a small aerosol concentration behind the filter probe can be reliably detected. In filter testing the level of penetrability of the filter is determined as the ratio of the aerosol concentration in front of and behind the filter. The light traps 35 are provided to avoid stray light caused by light reflections at the walls of the housing 1.

FIG. 7 elucidates an embodiment example of an universal scatter light measuring implement. Here also, several light sources 8, 9, 10, 11, 12 are provided, the angles can be changed relatively to FIG. 3 The beams of light from all light sources are directed towards one light-scattering center 2. The impulses of the light scatterer in direction of the axis 5 are received by the receiver 4. The control device 15 comprises the electrical power supply unit 17 a multiplexer 41 and an impulse generator 42, which are, in the shown manner, connected by lines with each other as well as with light sources 8, 9, 10, 11, 12. A microprocessor 43 as well as an A/D converter 44 which is connected with the receiver 4 are belonging to the evaluating device 16. A data line 45 connects the multiplexer 41 with the microprocessor 43.

With this universal scatter light measuring implement, the scatter light impulses can be received in forward as well as in backward scatter to use them for determining the size and the size distribution of the particles. The depicted ranges of angle are each provided with two monochromatic light sources 8, 9, 10, 11 or 12. The light sources emit beams of light of different wave lengths. Although only two light sources, for example light sources 8, are depicted in each case, further light sources 8 are provided which are arranged radial symmetrically around the axis of the tube section 13. The carrier medium with the particles flows through the tube section 13 in direction of the arrow 14. The scatter light impulses reach the receiver 4 in direction of the axis 5, the angle of view of the receiver 4 is restricted to the short-range around the axis of the tube section 13. The impulse generator 42 supplies an impulse on request of microprocessor 43, the width of the impulse establishes the operating time of the light sources 8, 9, 10, 11 or 12. With the aid of the multiplexer 41, the microprocessor 43 select s the light sources which shall be switched on during the impulse time. The light sources which are presently switched on illuminate the particles 3 situated in the light-scattering center 2 and scattering the light. The scatter light impulses are converted by the receiver 4 into electrical impulses the width of which is established by the operating time of the light sources. The scatter light impulses are amplified by an amplifier. The height of the impulse is a measure of the intensity of the scattered light. The A/D converter 44 supplies the digital value of the impulse height to the microprocessor 43 which also is a store. In this way, the microprocessor 43 switches on all light sources belonging to the same range of angle, for example all light sources 8 or all light sources 9, during an impulse time. Herein, those light sources which have the same wave length can also be selected. With the next impulse the microprocessor 43 switches on other light sources of the same range of scattering angle having other wave lengths, for example other light sources 8. With the following impulse a change-over from the light sources 8 to the light sources 9 can take place, wherein again at first some of the light sources 9 having a first wave length and then other light sources 9 having other wave lengths are switched on. Each time the heights of the scatter light impulses are stored. Hence, the microprocessor stores the scatter light impulses from the respective light sources which are arranged at the respective angles in a cyclic order. After all light sources have been run through, the microprocessor 43 calculates the size or the size distribution of the particles, respectively, by means of the scatter light theory, and gives out the result. Then, the cyclic sequence can be repeated. The impulse sequence of the cyclic sequence is high in comparison with the stay time of the particles 3 in the light-scattering center 2. This means, that a plurality of scatter light impulses can be called up from one particle 3 and stored.

While preferred embodiments of the invention have been illustrated and described, it will be understood by those skilled in the art that variations and modifications thereof can be made without departing from the spirit and scope of the invention as set forth in the following claims.

I claim:

1. Apparatus for determining the density, size or size distribution of particles (3) suspended in a carrier medium by measuring the light scatter of the particles, the apparatus comprising:

at least one light source (8, 9, 10, 11, 12) which directs beams of light towards a light-scattering center (2) in a carrier medium having particles (3) suspended therein;

a first receiver (4) having a central axis (5) and for receiving at least a portion of the light scattered from the light-scattering center (2);

an evaluating device (16) connected downstream of the receiver (4), an elongated detection chamber having a central axis bounded radially by a wall of a housing (1), said housing (1) constructed to form a duct for the carrier medium with the particles to flow therethrough, wherein said each at least one light source (8, 9, 10, 11, or 12) is positioned substantially near the wall of the housing (1) and emits light toward the central axis of the detection chamber so that the light-scattering center (2) is formed in a region around the central axis of the detection chamber, said axis (5) of the first receiver (4) is coaxial with the central axis of the detection chamber, and a diaphragm system having a receiver housing (6) and a diaphragm (7) is associated with the first receiver (4) in such a way that the angle of view of the first receiver (4) does not cover the wall of the housing (1) surrounding the light-scattering center (2) but only a narrow region around the central axis of the detection chamber, characterized in that the housing (1) is formed by a tube section (13) and that the diaphragm system comprises an elongated receiver housing (6) which projects into the tube section (13), wherein the first receiver is arranged at a first end of the receiver housing (6) and a diaphragm (7) is arranged at its other end.

2. Apparatus according to claim 1, characterized in that the diaphragm system comprises several diaphragms (7) which are distributed within the receiver housing (6).

3. Apparatus according to claim 1, characterized in that said at least one light source (8, 9, 10, 11, or 12) comprises several light sources (8, 9, 10, 11, or 12) which are distributed in different positions substantially near the wall of the housing.

4. Apparatus according to claim 3, characterized in that at that said at least one light source (8, 9, 10, 11, or 12) comprises at least two light sources (8, 9, 10, 11, 12) which point at different angles to the axis (5) of the detection chamber and the first receiver (4).

5. Apparatus according to claim 4, characterized in that said at least one light source (8, 9, 10, 11, or 12) and said first receiver (4) are positioned wherein the first receiver (4) receives forward scattered and backward scattered light from the particles (3).

6. Apparatus according to claim 4, characterized in that said at least two light sources (8, 9, 10, 11 or 12) emit pulsed beams of light, and that a control device (15) provides for the timing of the pulsed beams of light and for controlling the assigning of each of said at east two light sources (8, 9, 10, 11, or 12) to an associated signal of the first receiver (4).

7. Apparatus according to claim 3, characterized in that at least two of said several light sources (8, 9, 10, 11, or 12) are directed towards a common light-scattering center (2).

8. Apparatus according to claim 1, characterized in that said at least one light source (8, 9, 10, 11, or 12) comprises at least two light sources (8, 9, 10, 11, or 12) which emit beams of light of different wave lengths.

9. Apparatus according to claim 1, characterized in that laser diodes or light emitting diodes are provided as said at least one light source (8, 9, 10, 11, or 12).

10. Apparatus according to claim 1, wherein the housing (1) is configured such that the carrier medium with the particles suspended therein flows substantially parallel to the central axis of the detection chamber at least from the light-scattering center (2) to the first end of the receiver housing (6) containing the first receiver (4).

11. Apparatus according to claim 1, further comprising:

a second receiver (4) having a central axis and for receiving at least a portion of the light scattered from the light-scattering center (2) and wherein the axis of the second receiver (4) is coaxial with the central axis of the detection chamber.

12. Apparatus according to claim 11, wherein the housing (1) is configured such that the carrier medium with the particles suspended therein flows substantially parallel to the central axis of the detection chamber at least from the first end of the receiver housing (6) containing the first receiver (4) to an end of a second receiver housing (6) containing the second receiver (4).

13. Apparatus for determining the density, size or size distribution of particles suspended in a carrier medium by measuring the light scatter from the particles, comprising:

a housing having a wall surface defining an elongated chamber having a longitudinal central axis extending therethrough, said housing being open at its ends and arranged to direct a carrier medium longitudinally therethrough;

a light receiver positioned concentric with said longitudinal axis, said light receiver including a plurality of light receiving diaphragms arranged to limit the light received by said light receiver to a field of view extending along said longitudinal axis and to exclude any light reflected by said surfaces of said housing;

at least one light source offset from said field of view oriented to direct a beam of light through said field of view and defining in said field of view a light scattering center for illuminating light scattering particles in the light scattering center; and an evaluating device connected to said light receiver for measuring the scattered light received by said light receiver from the light scattering particles in said light scattering center.

\* \* \* \* \*